(12) United States Patent
Buyuksahin (10) Patent No.: US 11,660,033 B2
(45) Date of Patent: May 30, 2023

(54) BIOMECHATRONIC DATA COMMUNICATION SYSTEMS

(71) Applicant: Utku Buyuksahin, Istanbul (TR)

(72) Inventor: Utku Buyuksahin, Istanbul (TR)

(*) Notice: Subject to any disclaimer, the term of this patent is extended or adjusted under 35 U.S.C. 154(b) by 966 days.

(21) Appl. No.: 16/331,037

(22) PCT Filed: Apr. 17, 2017

(86) PCT No.: PCT/TR2017/050146
§ 371 (c)(1),
(2) Date: Mar. 6, 2019

(87) PCT Pub. No.: WO2018/048369
PCT Pub. Date: Mar. 15, 2018

(65) Prior Publication Data
US 2019/0216328 A1    Jul. 18, 2019

(30) Foreign Application Priority Data
Sep. 9, 2016   (TR) .................................. 2016/12947

(51) Int. Cl.
*A61B 5/24*     (2021.01)
*A61B 5/00*     (2006.01)
(Continued)

(52) U.S. Cl.
CPC ................ *A61B 5/24* (2021.01); *A61B 5/307* (2021.01); *A61B 5/4029* (2013.01);
(Continued)

(58) Field of Classification Search
CPC ......... A61B 5/24; A61B 5/307; A61B 5/4029; A61B 5/6877; A61B 5/4851;
(Continued)

(56) References Cited

U.S. PATENT DOCUMENTS 7,883,536 B1    2/2011  Bendett et al.
2002/0075210 A1* 6/2002  Nestorovic ............ G02B 23/12
                                              359/356
(Continued)

FOREIGN PATENT DOCUMENTS

WO   2008136958 A1   11/2008
WO   2011057276 A2    5/2011
WO   2014011126 A1   10/2012

OTHER PUBLICATIONS

Lindsay, 'How the Phototransistor Circuit Works' learn.parallax.com; https://web.archive.org/web/20160422103717/https://learn.parallax.com/tutorials/robot/shield-bot/robotics-board-education-shield-arduino/chapter-6-light-sensitive-11 (Year: 2016).*
International Search Report and Written Opinion for corresponding PCT application No. PCT/TR2017/050146, dated Aug. 7, 2017.
International Preliminary Report on Patentability for corresponding PCT application No. PCT/TR2017/050146, dated Sep. 25, 2018.

*Primary Examiner* — Patrick Fernandes
(74) *Attorney, Agent, or Firm* — Notaro, Michalos & Zaccaria P.C.

(57) ABSTRACT

A data transmission system for transmitting an electrical data to a nerve cell. A data receiving system for receiving an electrical data from a nerve cell has at least two phototransistor crystals that is stimulated by light to form an electrical signal; an image source that allows the light to be sent to the phototransistor crystals and allows controlling the amount of light transmitted to each phototransistor crystal independently of each other, and at least one control unit that is connected to the image source that controls the amount of light transmitted from the image source to each of the phototransistor crystals.

28 Claims, 6 Drawing Sheets

(51) Int. Cl.
*A61B 5/307* (2021.01)
*G06F 3/01* (2006.01)
*A61F 2/68* (2006.01)

(52) U.S. Cl.
CPC .......... *A61B 5/6877* (2013.01); *A61B 5/4851* (2013.01); *A61B 5/6811* (2013.01); *A61B 2562/0209* (2013.01); *A61B 2562/0233* (2013.01); *A61B 2562/04* (2013.01); *A61B 2562/223* (2013.01); *A61F 2002/6827* (2013.01); *G06F 3/015* (2013.01)

(58) Field of Classification Search
CPC .......... A61B 5/6811; A61B 2562/0209; A61B 2562/0233; A61B 2562/04; A61B 2562/223; A61B 5/6868; A61B 5/0622; A61B 5/296; A61F 2002/6827; G06F 3/015; A61N 5/06; A61N 5/0622
See application file for complete search history.

(56) References Cited

U.S. PATENT DOCUMENTS

| | | | | |
|---|---|---|---|---|
| 2006/0276702 | A1* | 12/2006 | McGinnis | A61B 5/296 |
| | | | | 600/372 |
| 2007/0060984 | A1* | 3/2007 | Webb | A61N 5/0622 |
| | | | | 607/89 |
| 2007/0167815 | A1* | 7/2007 | Jacobsen | A61B 5/6868 |
| | | | | 600/459 |
| 2010/0121420 | A1* | 5/2010 | Fiset | A61N 5/06 |
| | | | | 607/94 |
| 2013/0046148 | A1* | 2/2013 | Tathireddy | A61N 5/0622 |
| | | | | 600/300 |

\* cited by examiner

BIOMECHATRONIC DATA COMMUNICATION SYSTEMS

TECHNICAL FIELD

The present invention relates to data communication systems that allow, for example, to receive an electrical data from a nerve cell and to transmit the electrical data to the nerve cell.

PRIOR ART

In a human body, data communication between the brain, spinal cord and other organs is achieved through nerve cells. The data received from the organs and the data transmitted to the organs are usually in the form of electrical signals. In addition, the data communication between the nerve cells is performed electrically or chemically.

Since the communication between the nerves and the organs is provided by electrical signals, it is also possible to transmit data from outside by nerves. For instance, in case of a person with limb loss, electrical signals can be transmitted to the nerve cells associated with the lost limb so as to mimic the data that should have been received from the lost limb. In this manner, for example, certain data from the prosthesis used by a patient suffering from hand loss can be transmitted to his brain through the patient's nerves.

In the known art, electrodes that are connected to nerve cells are used to transmit electrical signals to the nerve cells. However, since the nerve cells have very sensitive structures, the electrical signals sent to the nerve cell must be controlled very precisely. If the signal sent to the nerve cell has a relatively high voltage and/or current value, the nerve cell may get damaged whereby a high degree of pain may be felt. Furthermore, for example the need for individually controlling the electrical signal sent to each of the electrodes so as to send separate signals to a plurality of nerve cells, causes such systems to have complex, costly and large structures.

BRIEF DESCRIPTION OF THE INVENTION

With the present invention, there is provided a data transmission system that allows transmitting an electrical data to a target, and a data receiving system that allows receiving an electrical data from a target. Said data transmission system comprises at least two phototransistor crystals, each of which is stimulated by light, to form an electrical signal; at least one image source which allows the light to be sent to said phototransistor crystals and allows controlling the amount of light transmitted to each phototransistor crystal independently of each other; and at least one control unit which is connected to said image source and controls the amount of light transmitted from the image source to each of the phototransistor crystals. Each phototransistor crystal comprises at least one signal output at which electrical signal is generated and which is coupled to the target to which the generated electrical signal is to be transmitted; at least one voltage input common terminal; and at least one threshold light intensity control input which allows controlling the level of the electrical signal generated at the signal output according to the amount of light received.

Said data receiving system comprises at least two light crystals, each of which is connected to at least one target and emits light by means of an electric signal received from the corresponding target; at least one image sensor for detecting the light emitted by each light crystal independently of each other; and at least one control unit to which said image sensor is connected and to which the image generated by the image sensor is transmitted. Each light crystal comprises at least one signal input to which said target is connected and which receives the electrical signal received from the target; at least one threshold signal voltage control input which allows controlling the minimum value and level of the light generated in the light crystal according to the electrical signal received from the signal input; and at least one voltage input common terminal.

In the data transmission system according to the present invention, since an electrical signal is transmitted through the phototransistor crystal to a target such as a nerve cell, it is guaranteed that the transmitted electrical signal never exceeds a maximum value. Furthermore, by using a large number of phototransistor crystals and LCD panels, it is ensured that an electrical signal is sent individually to a plurality of targets. Similarly, in the data receiving system according to the present invention, thanks to using a large number of light crystals and image sensors, it is ensured that the electrical signal received from a plurality of targets is detected independently from each other. According to the data transmission system and the data receiving system of the present invention, the signal threshold value is also allowed to be able to be controlled by means of the threshold light intensity control input and the threshold signal voltage control input. Moreover, in the embodiments where the data transmission system and/or the data receiving system comprises an upper cover, the upper cover is fixed to nerve endings by micro-surgery with adhesion or a similar method. In the same way, it can be applied to the nerves of healthy individuals by means of the invention, therefrom it is made possible to send signals to their brain and/or receive the signals from their brain.

OBJECT OF THE INVENTION

An object of the present invention is to provide a data transmission system which allows transmitting electrical data individually to a plurality of nerve cells.

Another object of the present invention is to provide a data transmission system which allows transmitting an electrical data to a nerve cell.

Another object of the present invention is to provide a data receiving system which allows receiving the electrical data individually from the plurality of nerve cells.

Yet another object of the present invention is to provide a data receiving system which allows receiving an electrical data from a nerve cell.

Still another object of the present invention is to provide a data receiving system and a data transmission system, which are compact and easily controllable.

DESCRIPTION OF THE DRAWINGS

Illustrative embodiments of the data transmission system and the data receiving system according to the present invention are illustrated in the enclosed drawings, in which.

All the parts illustrated in the drawings are individually assigned a reference numeral and the corresponding terms of these numbers are listed as follows:

Phototransistor crystal (T)
Light crystal (P)
Nerve cell (N)
Sheath (M)
Light (l)
Signal output (1)
First conductive part (1a, 11a)
Second conductive part (8, 18)
Third conductive part (9, 19)
Threshold light intensity control input (2)
Voltage input common terminal (3, 13)
Image source (4)
Optical element (5, 15)
Body (6, 16)
Upper cover (7, 17)
Lower cover (10, 20)
Signal input (11)
Threshold signal voltage control input (12)
Image sensor (14)
Data input (21)
Data output (22)

DESCRIPTION OF THE INVENTION

In the cases of patients with limb loss, the nerve cells associated with said limb usually remain active. By using the active-remaining nerve cells, electrical signals can be sent to and/or received from the patient's brain. Therefore, with the present invention, there is provided a data transmission system which allows transmitting an electrical data to a target such as a nerve cell, and a data receiving system which allows receiving an electrical data from a target such as a nerve cell.

Figure 1:
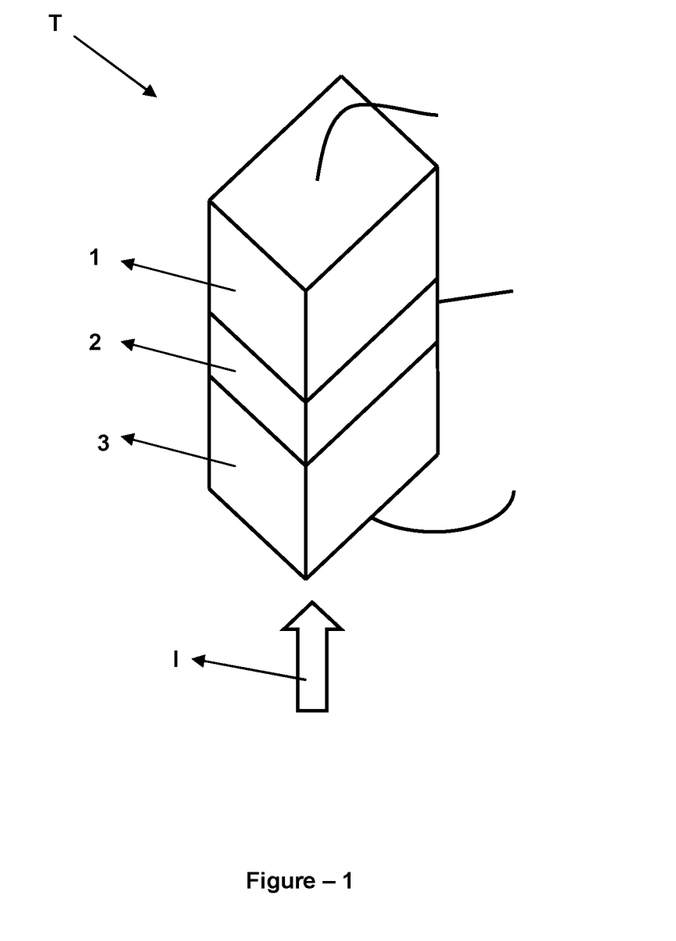
FIG. 1 is a perspective view of a phototransistor crystal that is used in the data transmission system according to the present invention.
Figure 2:
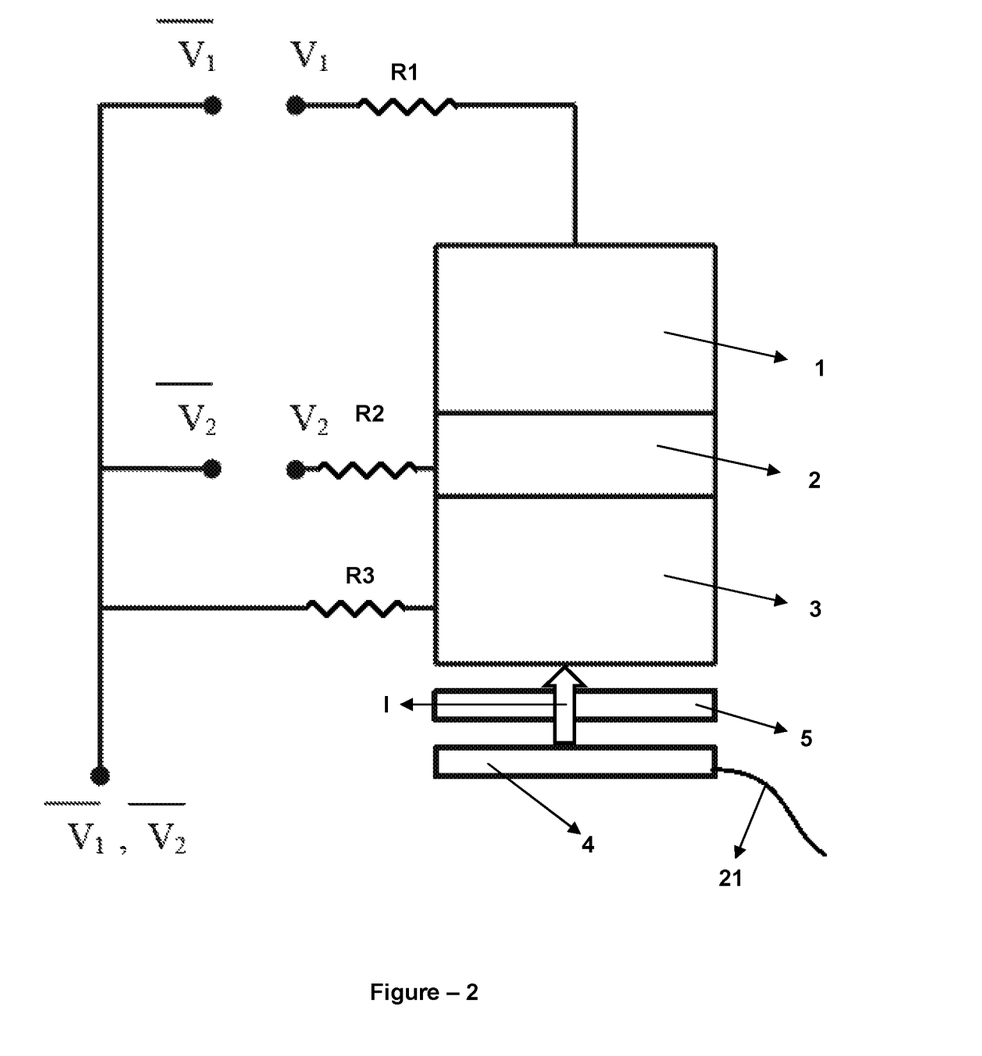
FIG. 2 is a view of a circuit diagram of the data transmission system according to the present invention.
Figure 3:
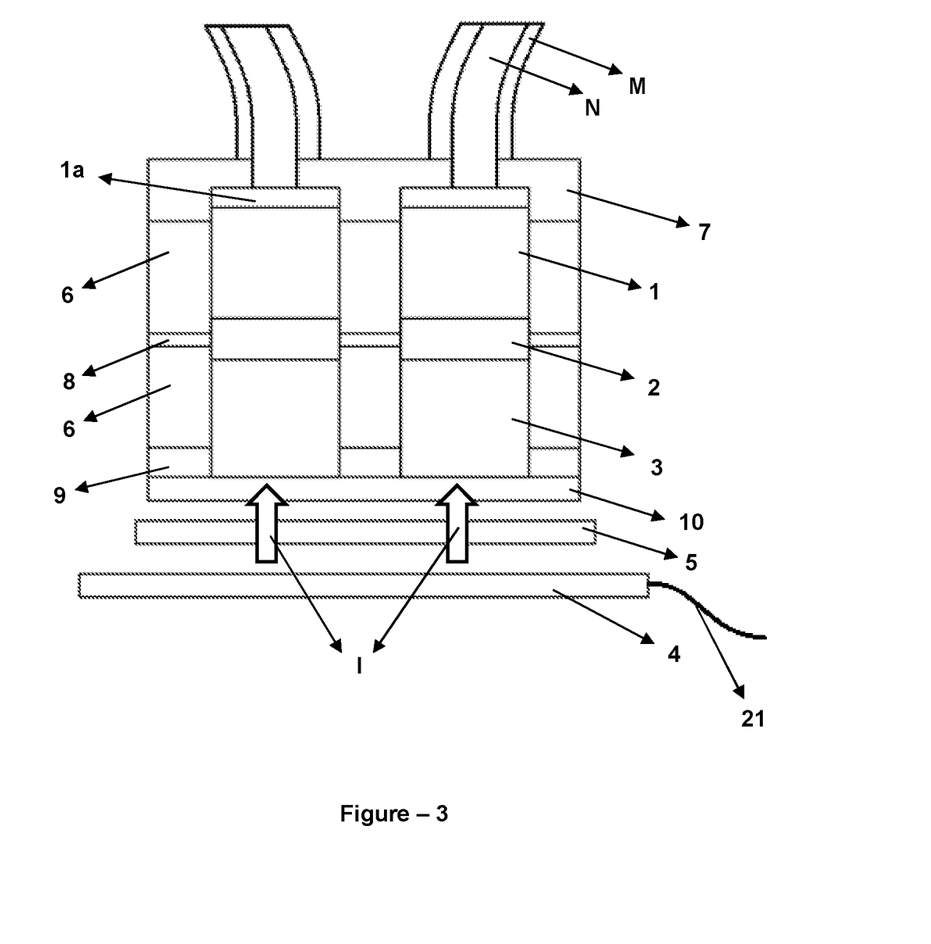
FIG. 3 is a view of an embodiment of the data transmission system according to the present invention.

The data transmission system according to the present invention, as illustrated in FIGS. 1-3, comprises at least two phototransistor crystals (T) which are stimulated by light (l) to form an electrical signal; at least one image source (4) (for example, LCD panel, OLED panel, screen etc.) which allows the light (l) to be sent to said phototransistor crystals (T) and allows controlling the amount of light (l) transmitted to each phototransistor crystal (T) independently of each other; and at least one control unit (not illustrated in Figures) which is connected to said image source (4) and controls the amount of light (l) transmitted from the image source (4) to each of the phototransistor crystals (T). Said phototransistor crystal (T) comprises at least one signal output (1) at which electrical signal is generated and which is coupled to the target to which the generated electrical signal is to be transmitted; at least one voltage input common terminal (3); and at least one threshold light intensity control input (2) which allows controlling the level of the electrical signal generated at the signal output (1) according to the amount of light (l) received. According to the invention, each pixel of the image source (4) serves as a separate light source. Here, since the image source (4) is able to transmit the light (l) individually to each phototransistor crystal (T), it is ensured that the electrical signal received from each phototransistor crystal (T) can be individually controlled in real time. Said image source (4) may have a structure that emits visible light (l), or may have a structure that emits the light (l) at an invisible frequency such as infrared or ultraviolet.

In an exemplary embodiment of the data transmission system, said phototransistor crystal (T) has a structure of an NPN or PNP transistor. The signal output (1) (N or P terminal) is connected to at least one nerve cell (N) as shown in FIG. 3. Said signal output (1) preferably comprises at least one first conductive part (1a), thereby it can be connected to the target easily so as to be able to transmit the electrical signals to the target. Here, the light (l) is transmitted onto the phototransistor crystal (T) by means of the image source (4) according to the data received from at least one data input (21) connecting the control unit and the image source (4) to each other. An electrical signal relative to the amount of transmitted light (l) is generated at the signal output (1), and the generated signal is transmitted to the nerve cell (N). In this manner, it is ensured that a desired electrical signal is sent to the nerve cell (N). Here, by virtue of controlling the brightness of the image source (4) by means of the control unit, the amount of light (l) falling on the phototransistor crystal (T) and thus the level of the electrical signal obtained at the signal output (1) are controlled. In this way, it is ensured that the signal transmitted to the nerve cell (N) is controlled. Thanks to a control signal sent from said threshold light intensity control input (2) (P or N terminal), the minimum values of the signal to be obtained at the signal output (1) can be controlled. Thus, for example, it is ensured that a signal is not obtained at the signal output (1) when the level of the light (l) received from the image source (4) is below a certain threshold value, whereas a signal is obtained at the signal output (1) when the level of the light (l) rises above said threshold value.

In a preferred embodiment of the invention, the data transmission system comprises at least one body (6) in which at least one phototransistor crystal (T) is positioned. Said body (6) is preferably in the form of an insulating gel. In this embodiment, the body (6) serves as an insulating layer to prevent the short circuit of the system and the damage of the phototransistor crystal (T) from environmental factors. In a preferred embodiment, said body (6) comprises at least one upper cover (7) for an easy connection of the phototransistor crystal (T) to a target. In an exemplary embodiment, said upper cover (7) is coupled to a sheath (M) (for example fascicle) located outside the nerve cell (N) so as to ensure that the nerve cell (N) is attached to the phototransistor crystal (T) in a firm and reliable manner. Said body (6) further comprises at least a second conductive part (8) connected with the threshold light intensity control input (2) so as to be able to send said control signal at the threshold light intensity control input (2). In another preferred embodiment, the body (6) comprises at least one lower cover (10) located on the side of the phototransistor crystal (T) that faces the image source (4). Said lower cover (10) has a transparent (light (l) transmitting) structure, which allows the light (l) rays coming from the image source (4) to reach the phototransistor crystal (T). In another preferred embodiment, the data transmission system comprises at least a third conductive part (9) to which the voltage input common terminal (3) of different phototransistor crystals (T) is connected.

The first conductive part (1a), the second conductive part (8) and the third conductive part (9) used in the system may be made of either conductive (zero electrical resistance) materials or the materials with an individual constant electrical resistance. In the alternative embodiments of the invention, by using conductors that have different electrical resistance values (R1, R2, R3) for the first conductive part (1a), the second conductive part (8) and the third conductive part (9), gain control of the phototransistor crystal (T) is able to be performed, the output voltage value is able to be controlled and/or limited to a fixed upper value. Furthermore, by using phototransistor crystals (T) made of different semiconductors (SiN, GeP etc.), maximum current and voltage limits required for the system can be achieved.

A circuit diagram of the data transmission system according to the present invention is shown in FIG. 2. Here, the signal obtained at the signal output (1) is indicated as V1, and the control signal sent to the threshold light intensity control input (2) is indicated as V2. The resistances indicated by R1, R2, R3 are the electrical resistance values of the first conductive part (1a), the second conductive part (8) and the third conductive part (9), respectively. Depending on the polarity of the signal generated in the embodiment (whether the phototransistor crystal (T) is NPN or PNP), the voltage V1 has a negative or positive polarity. Therefore, the polarity of the voltages that complete the circuit also changes according to the output polarity of the system. For this reason, instead of using the (+) or (−) sign in the electrical schemes, the voltage itself and its opposite (with reverse polarity) are shown. Those shown as overlined are "THE OPPOSITE" of the relevant voltages. In other words, if the polarity of Voltage V1 is Positive (+), its opposite is represented by the Negative (−) polarity. If the polarity of Voltage V1 is Negative (−), the opposite of V1 is represented by the Positive (+) polarity.

In a preferred embodiment of the invention, the data transmission system further comprises at least one optical element (5) disposed between the image source (4) and phototransistor crystals (T). Said optical element (5) preferably enables to match the phototransistor crystal (T) with the pixels of the image source.

In an exemplary embodiment of the invention, said data transmission system is used together with a tactile sensor (for example, a tactile sensor as explained in the patent document no. WO2014011126A1). In this embodiment, the control unit controls at what level the light (l) is to be sent to which phototransistor crystal (T) according to the tactile information (tactile position, intensity etc.) received from the touch sensor. Thus, the intensity and position of a touch via a prosthetic limb is, for example, able to be transmitted to the brain by means of the data transmission system developed in accordance with the present invention.

The control unit according to the invention can receive, by means of any wired or wireless data transfer method, the information concerning at what level the light (l) is to be sent to which phototransistor crystal (T). Thus, data is able to be sent to the brain of a person, to whom the invention is applied, either by means of the sensors of artificial devices such as prosthesis etc, attached on the person or by connecting with a remote device.

Although the data transmission system developed by the present invention is used for transmitting data to the nerve cells (N) in the examples hereinabove, the usage area of the data transmission system is not limited to only nerve cells (N). According to the data transmission system of the present invention, said data transmission system is able to be used in all the data transmission systems which require sensitive data transmission, since the level of the electrical signal received from the signal output (1) of the phototransistor crystal (T) (voltage value) is always below a maximum voltage value. Furthermore, in the embodiment wherein the data transmission system comprises a plurality of phototransistor crystals (T), the data transmission system developed by the present invention also provides a multi-channel data transmission, since the electrical signal received from each phototransistor crystal (T) can be individually controlled.

The electrical signals carried by the nerve cells (N) are transmitted as pulse width modulation (PWM) signal. In other words, the voltage value of the electrical signals carried by the nerve cells (N) is constant, and the frequency of the signal changes. Thus, in the embodiments wherein the data transmission system developed by the present invention is used particularly with the nerve cells (N), the electrical signal received from the signal output (1) of the phototransistor crystal (T) is also in the form of a PWM signal. In this embodiment, said control unit is also configured to control the frequency (flashing frequency) as well as the brightness level of the image source (4). Thus, it is ensured that the electrical signal received from the signal output (1) is controlled. In an exemplary embodiment, the brightness level of the light sent to each phototransistor crystal (T) is the same and by changing the flashing frequency of the light, the pulse width modulation of the electrical signal obtained from the each phototransistor crystal (T) is able to be controlled.

In another preferred embodiment of the invention, instead of matching each pixel of said image source (4) with a phototransistor crystal (T), a phototransistor crystal (T) is matched with more than one pixels. Thus, the amount of light (l) sent to the phototransistor crystal (T) can be increased and/or controlled more precisely.

In another preferred embodiment of the invention, said phototransistor crystal (T) has a structure of a phototransistor. Thus, it is made possible that the currently available phototransistors are used in the data transmission system of the present invention.

Figure 4:
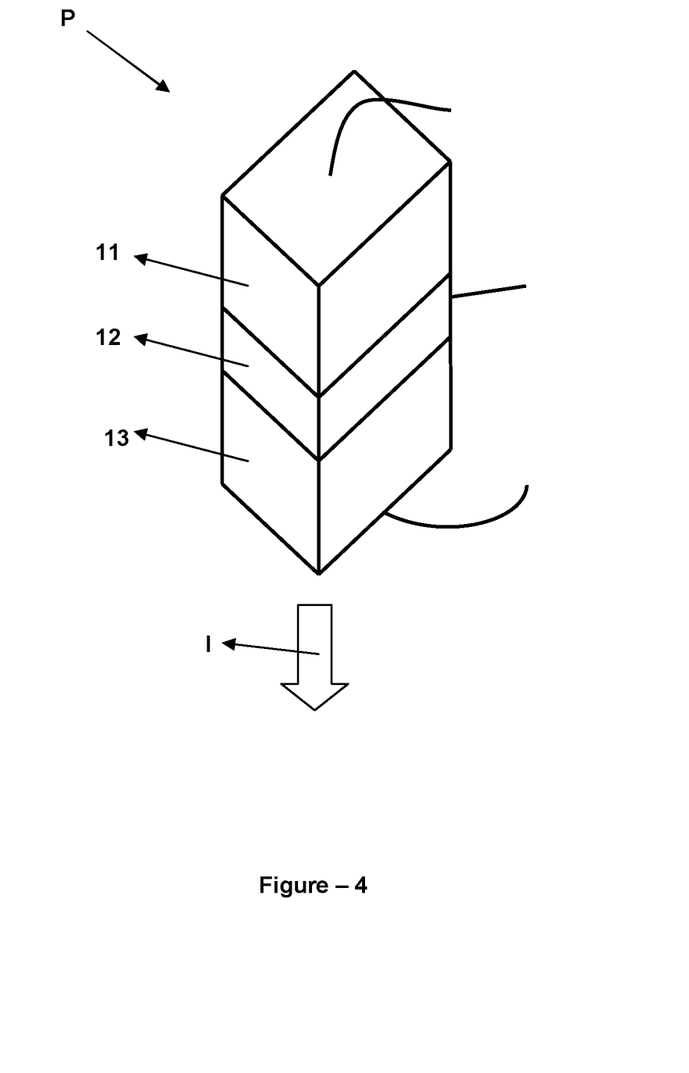
FIG. 4 is a perspective view of a light source that is used in the data receiving system according to the present invention.
Figure 5:
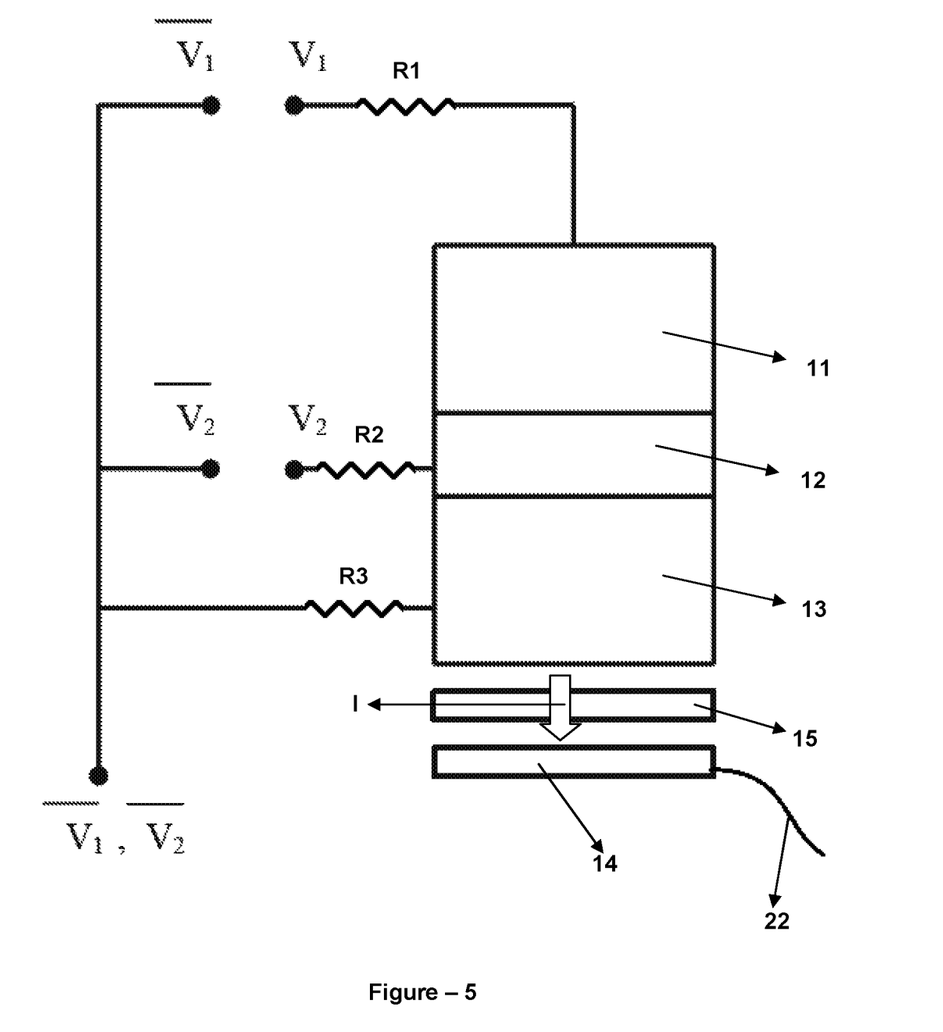
FIG. 5 is a view of a circuit diagram of the data receiving system according to the present invention.
Figure 6:
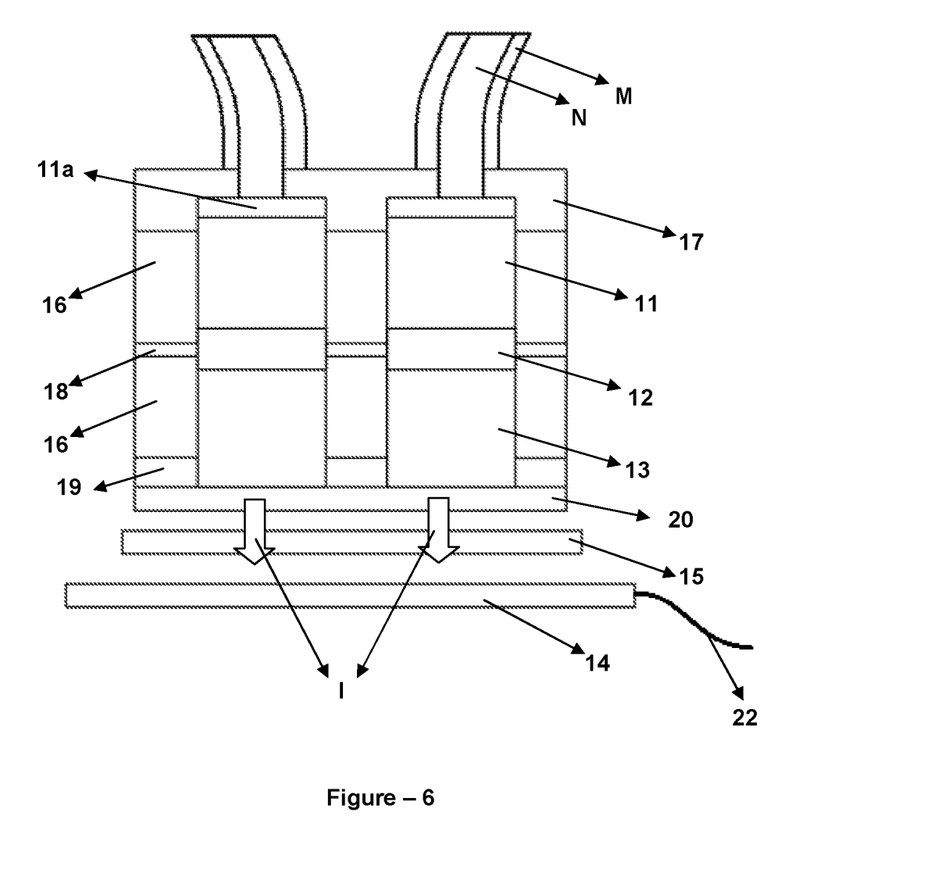
FIG. 6; is a view of an embodiment of the data receiving system according to the present invention.

The data receiving system according to the present invention, as illustrated in FIGS. 4-6, comprises at least two light crystals (P), each of which is connected to at least one target and emits light (l) by means of an electric signal received from the corresponding target; at least one image sensor (14) (for example, CMOS, CCD etc.) for detecting the light emitted by each light crystal (P) independently of each other; and at least one control unit (not shown in figures), to which said image sensor (14) is connected and to which the image generated by the image sensor (14) is transmitted preferably by means of at least two data outputs (22). Said light crystal (P) comprises at least one signal input (11) to which said target is connected and which receives the electrical signal received from the target; at least one threshold signal voltage control input (12) which allows controlling the minimum value and level (brightness) of the light generated in the light crystal (P) according to the electrical signal received from the signal input (11); and at least one voltage input common terminal (13). Said light crystal (P) may preferably have a structure, (for example a LED structure), that emits visible or invisible light (l) (such as infrared or ultraviolet). Here, it is ensured that the light (l) emitted by each light crystal (P) can be individually detected in real time since the light (l) emitted by each light crystal (P) is detected individually by the image sensor (14).

In an exemplary embodiment of said data receiving system, the light crystal (P) basically has a structure of an NPN or PNP crystal (LED). The signal input (11) (N or P terminal) is connected to at least one nerve cell (N) as shown in FIG. 6. Said signal input (11) preferably comprises at least one first conductive part (11a), thereby it can be connected to the target easily so as to be able to transmit the electrical signals to the target. Here, light (l) is generated in the light crystal (P) by means of an electrical signal coming from the nerve cell (N). Since the generated light is detected by the image sensor (14), the characteristics of the signal coming from the nerve cell (N) are able to be obtained by the image sensor (14). Thanks to a control signal sent from said threshold signal voltage control input (12) (P or N terminal), maximum and minimum values of the brightness of the light which is to be obtained in the light crystal (P) can be controlled. Thus, for example, it is ensured that no light is obtained in the light crystal (P) when the electrical signal received from the nerve cell (N) is below a certain threshold value, whereas a light is obtained in the light crystal (P) when the electrical signal rises above said threshold value.

In another preferred embodiment of the invention, the data receiving system comprises at least one body (16) in which at least one light crystal (P) is positioned. Said body (16) is preferably in the form of an insulating gel. In this embodiment, the body (16) serves as an insulating layer to prevent the short circuit of the system and the damage of the light crystal (P) from environmental factors. In a preferred embodiment, said body (16) comprises at least one upper cover (17) for an easy connection of the light crystal (P) to a target. In an exemplary embodiment, said upper cover (17) is coupled to a sheath (M) (for example fascicle) located outside the nerve cell (N) so as to ensure that the nerve cell (N) is attached to the light crystal (P) in a firm and reliable manner. Said body (16) further comprises at least a second conductive part (18) connected with the threshold signal voltage control input (12) so as to be able to send said control signal at the threshold signal voltage control input (12). In another preferred embodiment, the body (16) comprises at least one lower cover (20) located on the side of the light crystal (P) that faces the image sensor (14). Said lower cover (20) has a transparent (light (l) transmitting) structure, which allows the light (l) rays coming from the light crystal (P) to reach the image sensor (14). In another preferred embodiment, the data receiving system comprises at least a third conductive part (19) to which the voltage input common terminal (13) of different light crystals (P) is connected.

The first conductive part (11a), the second conductive part (18) and the third conductive part (19) used in the system may be made of either conductive materials (zero electrical resistance) or the materials with an individual constant electrical resistance. In the alternative embodiments of the invention, by using conductors that have different electrical resistance values (R1, R2, R3) for the first conductive part (11a), the second conductive part (18) and the third conductive part (19), gain control of the phototransistor is able to be performed and the output voltage value is able to be controlled and or limited to a fixed upper value. Furthermore, by using light crystals (P) made of different semiconductors (Si, GaSb, GaAs, SiGe etc.), current and voltage limits required for the system can be achieved.

A circuit diagram of the data receiving system according to the present invention is shown in FIG. 5. Here, the signal coming to the signal input (11) is indicated as V1, and the control voltage sent to the threshold signal voltage control input (12) is indicated as V2. The resistances indicated by R1, R2, R3 are the electrical resistance values of the first conductive part (11a), the second conductive part (18) and the third conductive part (19), respectively. Depending on the polarity of the signal generated in the embodiment (whether the light crystal (P) is NPN or PNP), the voltage V1 has a negative or positive polarity. Therefore, the polarity of the voltages that complete the circuit also changes according to the output polarity of the system. For this reason, instead of using the (+) or (−) sign in the electrical schemes, the voltage itself and its opposite (with reverse polarity) are shown. Those shown as overlined are "THE OPPOSITE" of the relevant voltages. In other words, if the polarity of Voltage V1 is Positive (+), its opposite is represented by the Negative (−) polarity. If the polarity of Voltage V1 is Negative (−), the opposite of V1 is represented by the Positive (+) polarity.

In a preferred embodiment of the invention, the data receiving system further comprises at least one optical element (15) disposed between the image sensor (14) and light crystal (P). Said optical element (15) preferably enables to match the light crystal (P) with the pixels of the image sensor.

In another preferred embodiment of the invention, instead of matching each pixel of said image sensor (14) with a light crystal (P), a light crystal (P) is matched with more than one pixels. Thus, the amount of light (l) sent to the image sensor (14) can be increased and/or controlled more precisely.

Although the data receiving system developed by the present invention is used for receiving data from the nerve cells (N) in the examples hereinabove, the usage area of the data receiving system is not limited to only nerve cells (N). In the embodiment wherein the data receiving system of the present invention comprises a plurality of light crystals (P), the data receiving system developed by the present invention also provides a multi-channel data transmission, since the light (l) emitted by each light crystal (P) can be individually detected.

The electrical signals carried by the nerve cells (N) are transmitted as pulse width modulation (PWM) signal. In other words, the voltage value of the electrical signals carried by the nerve cells (N) is constant, and the frequency of the signal changes. Thus, in the embodiments wherein the data receiving system developed by the present invention is used particularly with the nerve cells (N), a light (l) which has a constant brightness but a variable frequency, and emitted by the light crystal (P) is obtained. Furthermore, the information of the signal received from the nerve cell (N) is obtained according to the frequency change amount of the light.

In an exemplary embodiment, the data transmission system and the data receiving system of the present invention can be used together. The connection therebetween can be in the form of a wired or wireless communication. In this embodiment, for example, when a neural disconnection occurs between the brain and an organ of a patient, the nerve cell ending connected to the brain is attached to the data receiving system so that the electrical signal coming from the brain is detected. By attaching the nerve cell ending that is connected to the organ to the data transmission system and sending the electrical signal detected by the data receiving system to the data transmission system, it is ensured that a command coming from the brain is sent to the organ.

In another exemplary embodiment, a nerve cell (N) may be in connection with both the data transmission system and the data receiving system. In this embodiment, said nerve cell (N) is connected not only to the signal input (11) of the light crystal (P) but also to the signal output (1) of the phototransistor crystal (T). Here, since both the signal input (11) of the light crystal (P) and the signal output (1) of the phototransistor crystal (T) are interconnected through the nerve cell (N), the electrical signal obtained at the signal output (1) of the phototransistor crystal (T) stimulates the light crystal (P) as well. Thus, in this embodiment, the control unit in the data receiving system and the control unit in the data transmission system are in connection with each other, and for detecting a signal received from the nerve cell (N) in the data receiving system, the electrical signal sent to the nerve cell (N) by the data transmission system is also taken into account. In this embodiment, bilateral data transmission (both receiving and transmitting data) can be achieved with the nerve cells (N). In the embodiment where a connection is established with a plurality of nerve cells (N), a plurality of light carriers (for example a fiber optic cable) can be used in matching each light crystal (P) with a pixel of the image sensor and in matching each phototransistor crystal (T) with a pixel of a LCD panel. Here, while a first fiber optic cable harness allows light (l) transmission between the light crystals (P) and the image sensor, a second fiber optic cable harness allows light (l) transmission between the phototransistors (T) and the LCD panel.

In the data transmission system and the data receiving system according to the present invention, energy levels of the received and the transmitted data are able to be controlled by said control units. Thus, for example in case of an application of a prosthetic limb which uses the data transmission system, the intensity of a detected touch is able to be transmitted to the nerve cell (N) by increasing, decreasing, locally turning on or turning off, and/or applying various filters by the control unit. In this manner, the user's feeling sensitivity can be increased or decreased. In another exemplary embodiment, a weak signal, for example due to a nerve damage, received from a nerve cell (N), can be increased by the control unit in the data receiving system so that it can be perceived more strongly. Thus, it is ensured that the data receiving system can also be used in the persons with neural disorders.

Thanks to the data receiving system of the present invention, it is ensured that the electrical signals carried by different nerve cells (N) in the body can be easily transferred to a computer or processor, saved and analyzed. Thus, for example, by comparing the data obtained from healthy individuals and individuals with specific diseases, the cause of the related diseases can be understood. Furthermore, by analyzing the electrical signals, many mysteries related to the brain and nervous system can also be cleared up.

With the data receiving and transmission system of the present invention, nerve impulses required for stimulating the organs can be artificially sent to these organs, or the signal sent can be detected and transmitted in any desired form. For example, by sending signals to beta cells in pancreas, insulin secretion can be achieved.

In addition, for example signals carried by certain nerves can be saved and, where necessary, the saved data can be transmitted to the nerve cells (N) by using the data transmission system developed by the present invention. In an exemplary embodiment, feelings such as touching, jarring, moving in a movie can be artificially transmitted to viewers by being recorded during shooting a film or added later. For example, the electrical signals generated in the nerve cells (N) by smelling can be copied and artificially presented to the individuals so that the smell is able to be transmitted digitally.

The data receiving system and the data transmission system according to the present invention can be used for transfer of analog voltage, digital I/O signal, PWM signal, the signals in CAN BUS or in any other communication protocol.

In the data transmission system according to the present invention, since an electrical signal is transmitted through the phototransistor crystal (T) to a target such as a nerve cell (N), it is guaranteed that the transmitted electrical signal never exceeds a maximum value. Furthermore, by using a large number of phototransistor crystals (T) and LCD panels, it is ensured that an electrical signal is sent individually to a plurality of targets. Similarly, in the data receiving system according to the present invention, thanks to using a large number of light crystals (P) and image sensors, it is ensured that the electrical signal received from a plurality of targets is detected independently from each other. According to the data transmission system and the data receiving system of the present invention, the signal threshold value is also allowed to be able to be controlled by means of the threshold light intensity control input (2) and the threshold signal voltage control input (12). Moreover, in the embodiments where the data transmission system and/or the data receiving system comprises the upper cover (7, 17), the upper cover (7, 17) is fixed to nerve endings by microsurgery with adhesion or a similar method. In the same way, it can be applied to the nerves of healthy individuals by means of the invention, therefrom it is made possible to send signals to their brain and/or receive the signals from their brain.

The invention claimed is:

1. A data transmission system for transmitting an electrical data to a nerve cell (N), characterized by comprising:
   at least two phototransistor crystals (T), each of which is stimulated by light (l) to form an electrical signal, and comprising:
   at least one signal output (1), at which an electrical signal is generated and which is configured to be coupled to the nerve cell (N) to which the electrical signal is to be transmitted,
   at least one voltage input common terminal (3), and
   at least one threshold light intensity control input (2) configured for controlling a level of the electrical signal generated at the at least one signal output (1) according to an amount of light (l) received, wherein the electrical signal is obtained at the at least one signal output (1) only when a level of the light (l) rises above a threshold value,
   at least one image source (4) configured for sending the light (l) to the at least two phototransistor crystals (T) and configured for controlling the amount of light (l) transmitted to the at least two phototransistor crystals (T) independently of each other; and
   at least one control unit which is connected to said image source (4) and is configured to control the amount of light (l) transmitted from said at least one image source (4) to the at least two phototransistor crystals (T).

2. A data transmission system according to claim 1, characterized in that said at least one image source (4) has a structure that emits visible light (l).

3. A data transmission system according to claim 1, characterized in that said at least one image source (4) has a structure that emits infrared light (l).

4. A data transmission system according to claim 1, characterized in that said at least one image source (4) has a structure that emits ultraviolet light (l).

5. A data transmission system according to claim 1, characterized in that said at least one signal output (1) comprises at least one first conductive part (1a).

6. A data transmission system according to claim 1, characterized by comprising at least one data input (21) connecting the at least one control unit and the at least one image source (4) to each other.

7. A data transmission system according to claim 1, characterized by comprising at least one body (6) in which said at least two phototransistor crystals (T) are positioned.

8. A data transmission system according to claim 7, characterized in that the at least one body (6) comprises at least one upper cover (7) configured to connect the at least two phototransistor crystals (T) to the nerve cell (N).

9. A data transmission system according to claim 7, characterized in that the at least one body (6) comprises at least a conductive part (8) connected with threshold light intensity control input (2).

10. A data transmission system according to claim 7, characterized in that said at least one body (6) comprises at least one lower cover (10) located on a side of the at least two phototransistor crystals (T) that faces the at least one image source (4).

11. A data transmission system according to claim 10, characterized in that said at least one lower cover (10) has a transparent structure.

12. A data transmission system according to claim 7, characterized by comprising at least one conductive part (9) to which the at least one voltage input common terminal (3) of said at least two phototransistor crystals (T) is connected.

13. A data transmission system according to claim 1, characterized by comprising at least one optical element (5) disposed between the at least one image source (4) and the at least two phototransistor crystals (T).

14. A data transmission system according to claim 1, characterized in that each of said at least two phototransistor crystals (T) is matched with more than one pixels of the at least one image source (4).

15. A data receiving system for receiving an electrical data from at least two nerve cells (N), characterized by comprising:
  at least two light crystals (P), each of which is configured to be connected to one of said at least two nerve cells (N) and emits light (l) by means of an electric signal received from the one of said at least two nerve cells (N), and comprising:
  at least one signal input (11) to which said one of said at least two nerve cells (N) is configured to be connected and which is configured to receive the electrical signal received from the one of said at least two nerve cells (N),
  at least one threshold signal voltage control input (12) configured for controlling a maximum value and a minimum value and level of the light (l) generated in the at least two light crystals (P) according to the electrical signal received from the at least one signal input (11), wherein the light is obtained in one of the at least two light crystals (P) only when the electrical signal rises above a threshold value, and
  at least one voltage input common terminal (13),
  at least one image sensor (14) configured for detecting the light (l) emitted by each of said at least two light crystals (P) independently of each other; and
  at least one control unit to which said at least one image sensor (14) is connected and to which an image generated by the at least one image sensor (14) is transmitted.

16. A data receiving system according to claim 15, characterized in that said at least two light crystals (P) have a structure that emits visible light (l).

17. A data receiving system according to claim 15, characterized in that said at least two light crystals (P) have a structure that emits infrared light (l).

18. A data receiving system according to claim 15, characterized in that said at least two light crystals (P) have a structure that emits ultraviolet light (l).

19. A data receiving system according to claim 15, characterized in that said at least one signal input (11) comprises at least one first conductive part (11a).

20. A data receiving system according to claim 15, characterized by comprising at least one data output (22) connecting the at least one control unit and the at least one image sensor (14) to each other.

21. A data receiving system according to claim 15, characterized by comprising at least one body (16) in which said at least two light crystals (P) are positioned.

22. A data receiving system according to claim 21, characterized in that said at least one body (16) comprises at least one upper cover (17) configured to connect said at least two light crystals (P) to said at least two nerve cells (N).

23. A data receiving system according to claim 21, characterized in that said at least one body (16) comprises at least a conductive part (18) connected with threshold light signal voltage control input (12).

24. A data receiving system according to claim 21, characterized in that the at least one body (16) comprises at least one lower cover (20) located on a side of the at least two light crystals (P) that faces the at least one image sensor (14).

25. A data receiving system according to claim 21, characterized in that said at least one lower cover (20) has a transparent structure.

26. A data receiving system according to claim 21, characterized by comprising a conductive part (19) to which the at least one voltage input common terminal (13) of said at least two light crystals (P) is connected.

27. A data receiving system according to claim 15, characterized by comprising at least one optical element (15) disposed between the at least one image sensor (14) and the at least two light crystals (P).

28. A data transmission system according to claim 1, wherein the at least one image source is at least one pixel of a LCD panel, OLED panel, or screen.

* * * * *